United States Patent [19]
Miller

[11] Patent Number: 5,314,123
[45] Date of Patent: May 24, 1994

[54] ELECTROSTATIC SPRAYING

[75] Inventor: Paul C. H. Miller, Haynes, England

[73] Assignee: British Technology Group Ltd., London, England

[21] Appl. No.: 550

[22] Filed: Jan. 4, 1993

Related U.S. Application Data

[63] Continuation of Ser. No. 839,698, Feb. 21, 1992, abandoned, which is a continuation of Ser. No. 634,187, filed as PCT/GB89/00814, Jul. 14, 1989, abandoned.

[30] Foreign Application Priority Data

Jul. 15, 1988 [GB] United Kingdom ............ 8816906

[51] Int. Cl.⁵ .................................................. B05B 5/02
[52] U.S. Cl. ........................................ 239/708; 239/120
[58] Field of Search ............... 239/690, 690.1, 706, 239/707, 120, 121, 708

[56]  References Cited

U.S. PATENT DOCUMENTS

| | | | |
|---|---|---|---|
| 3,211,377 | 10/1965 | Brenner | 239/121 X |
| 4,004,733 | 1/1977 | Law . | |
| 4,239,157 | 12/1980 | Fasthh | 239/121 X |
| 4,498,626 | 2/1985 | Pitchford | 239/600 X |

FOREIGN PATENT DOCUMENTS 1251437 12/1960 France .
2317016 2/1977 France .
2192351 1/1988 United Kingdom .

Primary Examiner—Andres Kashnikow
Assistant Examiner—Kevin P. Weldon
Attorney, Agent, or Firm—Cushman, Darby & Cushman

[57] ABSTRACT

A spray arrangement including means to form and direct a spray of liquid droplets and means to apply an electrostatic charge to droplets in said spray, said charge applying means including an insulating body to support a spray-charging electrode in association with the spray-forming means, the spray-forming means [10] forming the spray hydraulically, the body [20] having a smoothly-constricted bore [26, 27, 28] for the free passage of spray with the electrode [23] housed to expose only inward-facing electrode surface [28] as the constriction to passing spray [40] for the acquisition of charge therefrom, the bore surface turning back upon itself [29] as it expands beyond the constriction to form an end of the body, the end of the body where the surface turns back upon itself [29] and the part of the bore remote from said end being formed to assist the shedding of liquid [22, 51, 52]. The arrangement is suitable as a dairy sprayer to direct charged spray upwardly from said turned-back end on to the teats and udder of a dairy animal such as a cow, ewe or goat.

8 Claims, 1 Drawing Sheet

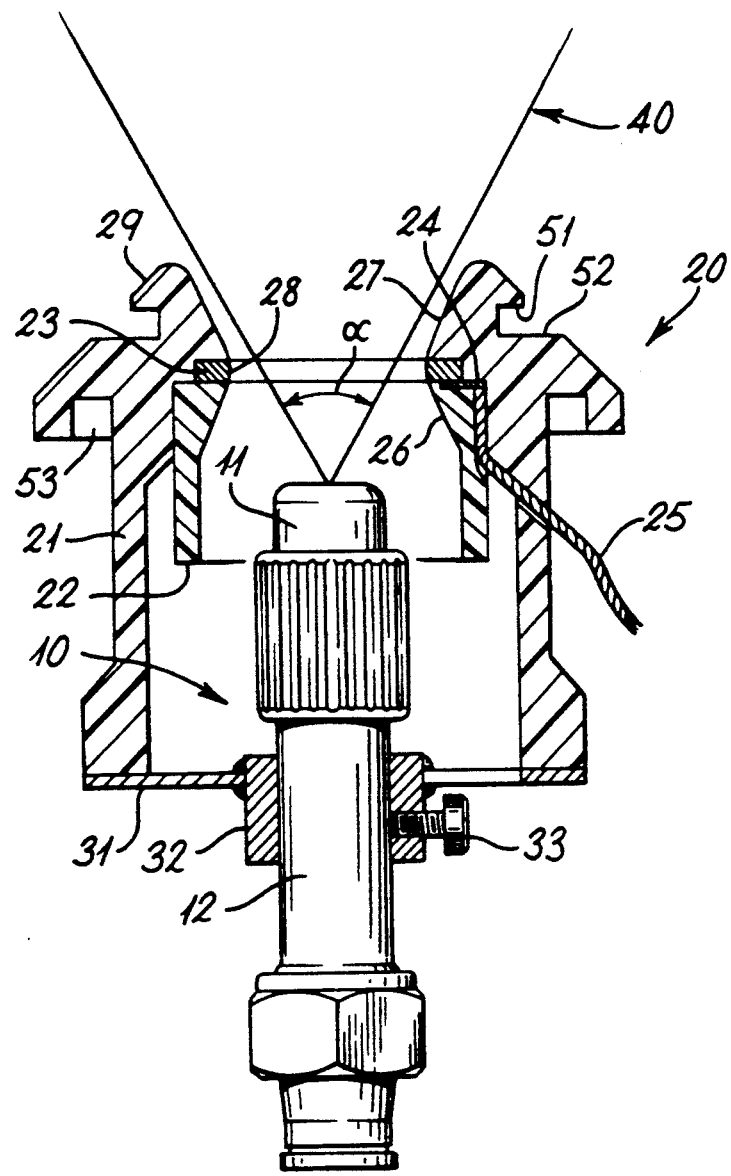

ELECTROSTATIC SPRAYING

This is a continuation of application Ser. No. 07/839,698, filed on Feb. 21, 1992, now abandoned; which is a continuation of 07/634,187 filed as PCT/GB89/00814, Jul. 14, 1989, now abandoned.

BACKGROUND OF THE INVENTION

1. Field of the Invention

This invention relates to electrostatically charged sprays and more particularly to sprays for the teats and udder of cows and like milk-producing animals.

2. Description of the Art

When cows are milked it is desirable to clean and/or disinfect the teats and udder. This can be done by wiping with a cloth carrying a suitable liquid disinfectant or other chemical, as is well known. In particular it is useful to apply a chemical to prevent the bacterial infection which can occur after milking as the teat duct is then still open. One technique is to dip the teats, usually singly, into a dip-cup of chemical. This is clearly a tedious operation and errors can occur while excess chemical will drip off. A fine spray of suitable liquid may be used instead. Whatever the liquid or technique used there is a need for the accurate deposition of liquid on the teats and udder of a cow, while avoiding the deposition of the liquid elsewhere, both to avoid waste and possible pollution or adverse effects. In particular an unbroken ring of chemical around the end of the teat to exclude bacteria moving over the surface is required. It has already been proposed that electrostatically charged sprays be used, e.g. U.K. Published Patent Application 2192351A in which a flow of air is provided in addition to the spray of liquid to counter the fall-back of spray liquid from the upwardly-directed spray. However, such proposals, although providing an improvement on earlier techniques, still have problems. One problem is that the need for even a small amount of air flow is a complication.

SUMMARY OF THE INVENTION

It is an object of the present invention to provide an electrostatic spray technique, particularly for dairy use, which mitigates the problems set out above.

According to the invention there is provided a spray arrangement including means to form and direct a spray of liquid droplets and means to apply an electrostatic charge to droplets in said spray, said charge applying means including an insulating body to support a spray-charging electrode in association with the spray-forming means, the spray-forming means forming the spray hydraulically, the body having a smoothly-constricted bore for the free passage of spray with the electrode housed to expose only inward-facing electrode surface as the constriction to passing spray for the acquisition of charge therefrom, the bore surface turning back upon itself as it expands again beyond the constriction to form an end of the body, the end of the body where the surface turns back upon itself and the part of the bore remote from said end being formed to assist the shedding of liquid landing thereon.

Advantageously the spray arrangement is a dairy sprayer to direct spray upwardly on to the teats and udder of a dairy animal such as a cow, ewe or goat. The spray may be applied to the udder and teats in milking procedures. No air supply is needed.

Preferably the means to form a spray of liquid is a nozzle which forms a hollow cone-shaped spray and the nozzle is positioned so that the spray cone just passes the inward-facing electrode surface. Advantageously the spray cone breaks into droplets just beyond the electrode.

Conveniently the electrode is a ring of metal, the spray, in operation, being directed through the ring.

According to the invention there is also provided a method of charging a spray for the udder of a dairy animal including hydraulically producing an upwardly directed spray with a continuous liquid portion and a droplet portion, positioning a charging electrode beyond where the spray is produced with only the inner surface exposed to said spray and before the continuous portion becomes the droplet portion, causing said spray to pass the electrode inner surface and applying a charging potential between the electrode and the spray liquid.

BRIEF DESCRIPTION OF THE DRAWING

Embodiments of the invention will now be described with reference to the accompanying drawing which shows, partly in cross-section, a spray arrangement particularly suitable for dairy use.

DETAILED DESCRIPTION OF THE PRESENTLY PREFERRED EXEMPLARY EMBODIMENT

On a spray forming nozzle indicated generally at 10 is mounted an insulating body, indicated generally at 20, for example by a metal spider 31 and boss 32 including a clamp screw 33. This permits the insulating body to be moved along the nozzle stem 12, as explained below. Also the mounting conveniently provides an electrical earth or earthy terminal for the charging process.

The nozzle tip 11, for forming a spray of droplets, can be of conventional type to produce a cone 40 of spray droplets of known, stable included angle a. One suitable type is that used for domestic garden sprayers in which a cup-like cover having a small hole in the middle of the base of the cup is screwed onto a stem, for axial adjustment. The stem has a terminal boss with an inclined slit to allow pressurised liquid to enter the cup. Depending on the relative position of the cup and boss the liquid emerges from the small hole as a spray or jet. The cup is therefore set to give a spray of the required hollow conical form at the pressure of the liquid supplied. Other types of spray-forming means can of course be used, including those to produce a solid cone.

The body 20 is of a suitable insulating material such as plastics and shaped by moulding, machining or other convenient means. Certain parts of the body 20 need to be of closely-controlled specific shape. For this reason, and to simplify the inclusion of an electrode, 23, and connector 24, 25, the body is conveniently in two parts 21, 22. Through body 20 is a smoothly-constricted bore formed by the inside 26 of part 22, the inward-facing surface 28 of electrode 23 as the actual construction and the inside 27 of part 21. Importantly the inside surface 28 of electrode 23 is smoothly included into the bore. As the bore expands again at 27 beyond the constriction at electrode 23 it turns back on itself as it continues to expand forming outer conical surface 29 of body part 21. This outer conical surface 29 is conveniently provided with features to assist the shedding of spray liquid landing thereon and resist the formation of electrical breakdown paths. Such features include the edge 51 and the cut-away portions 52, 53. The skirt formed by part 22 also assists the shedding of liquid and increases the surface distance from electrode 23 to the metal part 31.

The electrode 23 mentioned above is a metal ring trapped between the two parts 21 and 22 with a suitable electrical connection 24 and lead 25. The charging process is by induction between electrode 23, energised to some 3 to 5 kilovolts, and the liquid from nozzle 10 which is earthed or earthy. This condition of earthed or earthy can be achieved in various ways known to those skilled in the art such as using a conductive liquid and earthing the supply container or making the nozzle conductive and connecting it to earth for example through the metal spider and boss 32.

The spacing of the outlet from the nozzle and the electrode 23 and the spray cone angle α can greatly affect the charging action. The spray cone is positioned to diverge through the electrode. Clearly the spray cone angle α must be such that spray does not hit the surfaces 27 or 28. The spray cone has two parts, a continuous liquid part and a droplet part. So far the best results have been with the nozzle outlet behind the electrode so that the edge of the continuous part of the cone is by the electrode. In this way the nozzle tip 11 is as far as possible from the electrode while the liquid part of the cone is as close as possible. This arrangement is believed to give greatly improved charging. The expanding bore, particularly the surface 27 is believed to reduce the risk of a virtual electrode being induced in this region.

In one series of tests a plastic nozzle was used. It was found that nozzles of the same type had varying performance and accordingly one nozzle was left set at a suitable spray cone form for the tests. The nozzle was axially adjusted so that the spray cone provided by the nozzle was just completely clear of the electrode. The voltage applied between the electrode and the earth point was 5 KV and a current of up to 2 milliamperes was available.

The spray droplet median diameter in these tests was about 240 micrometers.

Measurement of the charge to mass ratio at 5 KV electrode voltage gave a value of 0.65 millicoulombs/kilogram for tap water at a nozzle flow rate of 6.25 milliliters/second and a liquid supply pressure of 3.1 bar. When 0.1% of surfactant was added (AGRAL(RTM)-ICI plc), as is needed in practice for wetting, and a covering of silicone grease applied to the electrode to offset the action of the surfactant the value became 0.56 mC/kg. The silicone grease improved electrical stability. If the electrode voltage is reduced there is a linear reduction in charge to mass ratio.

A test was made on a simulated udder and teats, with the nozzle static and spraying charged spray upwards from 40 centimeters below the actual udder (that is ignoring the length of the teats). A timed pulse of spray was used to give a repeatable test. This test revealed a very good uniformity of spray deposit around the simulated teats, as determined by fluorometric analysis, both on the surfaces "seen" by the nozzle and those "behind" the teat viewed from the nozzle. When uncharged spray was used only half the amount of spray deposited on the "inside" of the teat was deposited on the "outside" while the actual amount on the "inside" was half that for the charged spray. Subject to the fairly simple form of this test the charged spray was seen to be very much more effective at safely applying a uniform and predictable deposit on the teats and udder of a cow, or like animal.

Various practical forms of the arrangement are possible. For example in a static form, where the animal walks over the sprayer, two sprays of narrow cone angle could be directed towards each other to converge at the expected position of the udder and teats. At the convergence the similarly-charged spray clouds would repel each other and this would assist the deposit of spray liquid on the udder. To optimise spray deposition the sprayer could be activated by a sensor, in any convenient manner, to spray only the udder region, and for a specific time. For hand-held use, where the nozzle would be held closer under the animal and the user might not have a clear view of the udder, a wider cone angle might be better.

Other features of constuction and operation appropriate to electrostatically charged sprayers for agricultural use will be readily apparent to those skilled in the art. Clearly various forms of nozzle may be used.

The form of the insulating body and electrode and relative position of electrode and spray provide reliable, effective operation even when spraying upwards, as is needed to spray an udder and teats, and the spray device is resistant to failure caused by wetting with return spray liquid, as has hitherto been a problem unless extra purge air supplies were used. Good charge to mass ratio is achieved ensuring the effective use of electrostatic technique for even coverage and avoiding the waste of spray, and possible contamination.

What is claimed is:

1. A spray arrangement comprising:
    means for forming a spray of liquid droplets;
    means for directing said spray of liquid droplets; and
    means for applying an electrostatic charge to said liquid droplets;
    wherein said applying means includes a spray-charging electrode and an insulating body supporting said spray-charging electrode;
    wherein said insulating body includes a smoothly-constricted bore for allowing the free passage of spray therethrough, said constricted bore being formed at a smallest diameter region of said insulating body, with said electrode being housed within said insulating body at said constricted bore so that only an inward face of said electrode is exposed, said inward face defining an interior periphery of said bore, said inward face charging said spray as it passes through said constricted bore; and
    wherein said body includes a surface outside of said constricted bore that slopes away from said bore so as to shed liquid that lands thereupon.

2. An arrangement according to claim 1, wherein said arrangement is an electrostatic dairy sprayer with said forming means and said directing means including means disposed so as to direct said charged spray in an upwards direction so that said spray is incident upon the teats and udder of a dairy animal including cows, ewes and goats, and so as to have said sloping surface opposed to the teats and udder of a dairy animal.

3. An arrangement as claimed in claim 1, wherein the forming means is a nozzle which forms a hollow cone-shaped spray and the nozzle is disposed so that the hollow cone-shaped spray just passes the inward face of the electrode.

4. An arrangement according to claim 1, wherein the forming means is a nozzle supported spaced back from the electrode in the bore, said bore tapering outwards as the bore approaches said sloped surface.

5. An arrangement according to claim 1 wherein the electrode is a ring of metal, the spray, being directed through the ring.

6. A method for charging a spray for the udder of a dairy animal, comprising the steps of:
   hydraulically producing a spray with a continuous hollow cone shaped droplet pattern;
   directing said spray toward the udder of said dairy animal;
   allowing said spray to pass through a bore being smoothly tapered toward an outlet constriction;
   providing an electrode in a wall of said bore at said outlet constriction so that only an inner face of said electrode is exposed;
   causing said spray to pass said inner face; and
   applying a charging potential between said electrode and said spray.

7. A method according to claim 6 including causing the spray cone to break into droplets just beyond the electrode.

8. A method according to claim 6, further comprising the step of draining excess liquid from said spray away from said bore by providing a surface sloping away from an interior of said bore.

* * * * *